United States Patent [19]

Hedgecock et al.

[11] Patent Number: 5,017,574
[45] Date of Patent: May 21, 1991

[54] NOVEL IMIDAZOBENZODIAZEPINES

[75] Inventors: Charles J. R. Hedgecock; Stuart D. Jones; Elizabeth A. Kuo, all of Swindon, United Kingdom

[73] Assignee: Roussel Uclaf, Paris, France

[21] Appl. No.: 516,194

[22] Filed: Apr. 26, 1990

[30] Foreign Application Priority Data

Apr. 27, 1989 [GB] United Kingdom ............... 8909700

[51] Int. Cl.$^5$ .................... C07D 487/04; A61K 31/55
[52] U.S. Cl. .................................... 514/220; 540/498
[58] Field of Search ........................ 540/498; 514/220

[56] References Cited

U.S. PATENT DOCUMENTS 4,868,176 9/1989 Gardner et al. .................... 540/498

Primary Examiner—Robert T. Bond
Attorney, Agent, or Firm—Bierman and Muserlian

[57] ABSTRACT

A compound selected from the group consisting of a compound of the formula

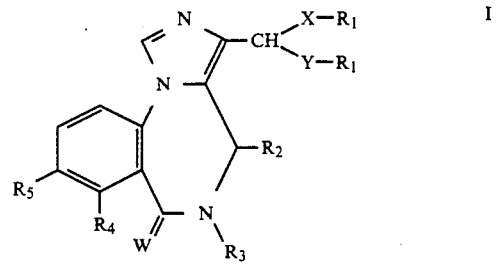

wherein the $R_1$s are the same and are alkyl of 1 to 3 carbon atoms or together are alkylene of 2 to 5 carbon atoms, X, Y and W are individually —O— or —S—, $R_2$ is hydrogen or alkyl of 1 to 3 carbon atoms, $R_3$ is selected from the group consisting of hydrogen, alkyl of 1 to 5 carbon atoms and phenyl optionally substituted with at least one member of the group consisting of halogen, alkyl and alkoxy of 1 to 3 carbon atoms and —$CF_3$, $R_4$ and $R_5$ are individually selected from the group consisting of hydrogen, halogen, —OH, alkyl and alkoxy of 1 to 3 carbon atoms and —$CF_3$ with the proviso that when $R_1$ and $R_2$ are alkyl, X and Y are the same and their non-toxic, pharmaceutically acceptable acid addition salts having benzodiazepine inverse agonist properties.

12 Claims, No Drawings

NOVEL IMIDAZOBENZODIAZEPINES

OBJECTS OF THE INVENTION

It is an object of the invention to provide the novel compounds of formula I and their non-toxic, pharmaceutically acceptable acid addition salts and a process for their preparation.

It is another object of the invention to provide novel compositions and method for inducing benzodiazepine inverse agonist activity in warm-blooded animals.

These and other objects and advantages of the invention will become obvious from the following detailed description.

THE INVENTION

The novel compounds of the invention are selected from the group consisting of a compound of the formula

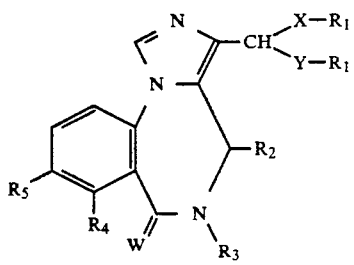

wherein the $R_1$s are the same and are alkyl of 1 to 3 carbon atoms or together are alkylene of 2 to 5 carbon atoms, X, Y and W are individually —O— or —S—, $R_2$ is hydrogen or alkyl of 1 to 3 carbon atoms, $R_3$ is selected from the group consisting of hydrogen, alkyl of 1 to 5 carbon atoms and phenyl optionally substituted with at least one member of the group consisting of halogen, alkyl and alkoxy of 1 to 3 carbon atoms and —CF$_3$, $R_4$ and $R_5$ are individually selected from the group consisting of hydrogen, halogen, —OH, alkyl and alkoxy of 1 to 3 carbon atoms and —CF$_3$ with the proviso that when $R_1$ and $R_2$ are alkyl, X and Y are the same and their non-toxic, pharmaceutically acceptable acid addition salts.

Examples of alkyl and alkoxy of 1 to 3 carbon atoms are methyl, ethyl, n-propyl, isopropyl, methoxy, ethoxy, propoxy and isopropoxy. Examples of alkyl of 1 to 5 carbon atoms are methyl ethyl, n-propyl, isopropyl, butyl, isobutyl, tert.-butyl or pentyl. Halogen includes fluorine, bromine or chlorine.

Examples of suitable acids for the preparation of the non-toxic, pharmaceutically acceptable acid addition salts are inorganic acids such as hydrochloric acid, hydrobromic acid, hydriodic acid, nitric acid, sulfuric acid, phosphoric acid, propionic acid, formic acid, benzoic acid, maleic acid, fumaric acid, succinic acid, tartric acid, citric acid, oxalic acid, glyoxylic acid, or aspartic acid, or alkanesulfonic acids such as methanesulfonic acid or arylsulfonic acids such as benzenesulfonic acid.

Among the preferred compounds of formula I are those wherein $R_3$ is methyl and those wherein W is oxygen, $R_2$ and $R_5$ are hydrogen and $R_4$ is —CF$_3$ or halogen and their non-toxic, pharmaceutically acceptable acid addition salts.

Specific preferred compounds of formula I are 5,6-dihydro-3-(1,3-dioxolan-2-yl)-5-methyl-imidazo-[1,5-a][1,4]-benzodiazepine-6-(4H)-one;

5,6-dihydro-3-(1,3-dithiolan-2-yl)-5-methyl-imidazo-[1,5-a][1,4]-benzodiazepine-6-(4H)-one;

5,6-dihydro-3-(1,3-dioxolan-2-yl)-5-methyl-7-trifluoromethyl-imidazo-[1,5-a][1,4]-benzodiazepine-6(4H)-one;

5,6-dihydro-5-methyl-3-(1,3-oxathiolan-2-yl)-7-trifluoromethyl-imidazo-[1,5-a][1,4]-benzodiazepine-6(4H)-one;

5,6-dihydro-5-methyl-3-(1,3-oxathiolan)-2-yl)-imidazo-[1,5-a][1,4]-benzodiazepine-6(4H)-one;

5,6-dihydro-7-fluoro-5-methyl-3-(1,3-oxathiolan-2-yl)-imidazo-[1,5-a][1,4]-benzodiazepine-6(4H)-one;

and their non-toxic, pharmaceutically acceptable acid addition salts.

The novel process for the preparation of compounds of the formula

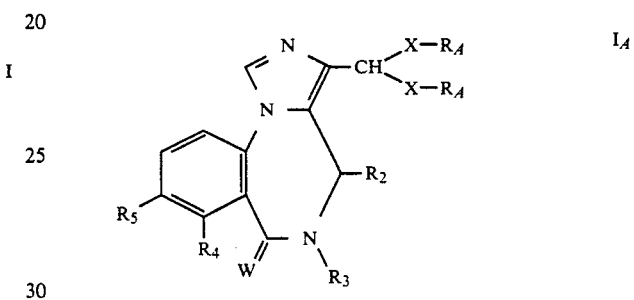

wherein $R_A$ is alkyl of 1 to 3 carbon atoms; and X, $R_2$, $R_3$, W, $R_4$ and $R_5$ are as defined above comprises reacting a compound of the formula

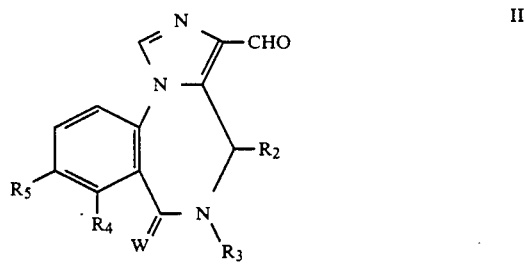

wherein $R_2$, $R_3$, W, $R_4$ and $R_5$ are as defined above with a compound of the formula

H—X—$R_A$  III wherein X and $R_A$ are as defined above.

The process of the invention for the preparation of compounds of the formula

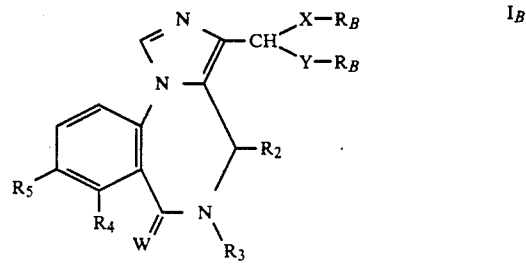

wherein the two $R_B$ groups together are alkylene of 2 to 5 carbon atoms and X, Y, $R_2$, $R_3$, W, $R_4$ and $R_5$ are as defined above comprises reacting a compound of formula II with a compound of the formula

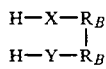

wherein X, Y and $R_B$ are as defined above.

The reactions between the compound of formula II and the compound of formula III, and between the compound of formula II and the compound of formula IV are preferably effected in the presence of an anhydrous organic solvent such as benzene or dichloromethane.

When a compound of formula II is reacted with a compound of formula III in which X is oxygen or with a compound of formula IV in which X and Y each are oxygen, the reaction is preferably effected in the presence of an anhydrous organic solvent such as benzene and in the presence of a catalytic quantity of p-toluene sulfonic acid at the reflux temperature of the reaction medium.

When a compound of formula II is reacted with a compound of formula III in which X is sulfur or with a compound of formula IV in which X and Y each is sulfur, the reaction is preferably effected in the presence of an anhydrous organic solvent such as dichloromethane in the presence of a catalytic quantity of boron trifluoroetherate at ambient temperature.

The compounds of formula II can be prepared, for example, as described in published European patent application No. 0,305,298.

The compounds of formula I are basic in character and may therefore be subsequently converted into their acid addition salts. The acid addition salts can be conveniently prepared by prepared by reacting, in approximately stoichiometric quantities, an inorganic or organic acid with a compound of formula I. The acid addition salts can be prepared without intermediate isolation of the corresponding base.

The compositions of the invention for inducing benzodiazepine inverse agonist activity are comprised of at least one compound of formula I and its non-toxic, pharmaceutically acceptable acid addition salts and an inert pharmaceutical carrier. The compositions may be in the form of tablets, dragees, capsules, granules, suppositories or injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions are useful for the treatment of memory problems, particularly in geriatrics, and in cerebral senescence problems. Some of the compositions also possess tranquiling activity and therefor can be used in the treatment of obesity and as minor tranquillizers in the treatment of certain agitated or irritated states and in some forms of epilepsy.

The novel method of the invention for inducing benzodiazepine inverse agonist activity in warm-blooded animals, including humans, comprises administering to warm-blooded animals an amount of at least one compound of formula I and its non-toxic, pharmaceutically acceptable acid addition salts to induce benzodiazepine inverse agonist activity. The compounds may be administered orally, rectally or parenterally and the usual daily dose is 0,0013 to 2,66 mg/kg depending on the specific compound, the condition treated and the method of adminstration.

In the following examples there are described several preferred embodiments to illustrate the invention. However, it should be understood that the invention is not intended to be limited to the specific embodiments.

EXAMPLE 1

5,6-dihydro-3-(1,3-dioxolan-2-yl)-5-methyl-imidazo[1,5-a][1,4]benzodiazepine-6(4H)-one 100 mg (0.46 mmol) of 5,6-dihydro-5-methyl-6-oxo-4H-imidazo[1,5-a][1,4]benzodiazepine-3-carboxaldehyde in 3 ml of benzene were refluxed with 0.1 ml of ethylene glycol and a catalytic amount of p-toluene sulfonic acid. After 5 hours, the solvent was removed and the product was taken in $CH_2Cl_2$ and washed with 5% sodium carbonate and water. After drying, 95 mg (73%) of 5,6-dihydro-3-(1,3-dioxolan-2-yl)-5-methyl-imidazo5,6-dihydro-3-(1,3-dioxolan-2-yl)-5-methyl-imidazo[1,5-a][1,4]benzodiazepine-6(4H)-one were obtained.

Preparation of 5,6-dihydro-5-methyl-6-oxo-4H-imidazo[1,5-a][1,4]benzodiazepine-3-carboxaldehyde A mixture of 1.0 g (3.3 mmol) of methyl 5,6-dihydro-5-methyl-6-oxo-4H-imidazo[1,5-a][1,4]benzodiazepine-3-yl-N-carbohydroxamate (prepared according to EP No. 88.402166.8) in 36 ml of dry THF at 0° C. was stirred with 96 mg (2.4 mmol) of lithium aluminium hydride. After 4 hours, the reaction mixture was allowed to warm to ambient temperature and stirred for 22 hours. Then, a further portion of 33 mg of $LiAlH_4$ was added. After 4 hours, excess $LiAlH_4$ was destroyed with saline solution. The organic layer was filtered, dried and evaporated to dryness to obtain 0.59 g (73.2%) of 5,6-dihydro-3-(1,3-dioxolan-2-yl)-5-methyl-imidazo[1,5-a][1,4]benzodiazepine-6-(4H)-one after chromatography over silica gel.

EXAMPLE 2

5,6-dihydro-3-(1,3-dithiolan-2-yl)-5-methyl-imidazo[1,5-a][1,4]benzodiazepine-6(4H)-one 1.96 g (8.14 mmol) of 5,6-dihydro-5-methyl-6-oxo-4H-imidazo[1,5-a][1,4]benzodiazepine-3-carboxaldehyde were dissolved in 25 ml of dry $CH_2Cl_2$ 1 ml (12 mmol) of ethane-1,2-dithiol and 0.2 ml of boron trifluoroetherate was added and after stirring for 24 hours at ambient temperature, further 0.5 ml (6 mmol) of dithiol was added. The reaction was stirred for 7 days and then diluted with $CH_2Cl_2$. The mixture was washed with 5% sodium carbonate, 5% sodium hydroxide and water and was dried over $MgSo_4$ to obtain an oil. Purification over silica gel and crystallization from ether yielded 1.95 (75% yield) of 5,6-dihydro-3-(1,3-dithiolan-2-yl)-5-methyl-imidazo[1,5-a][1,4]benzodiazepine-6(4H)-one as a white crystalline product.

EXAMPLE 3

5,6-dihydro-3-(1,3-dioxolan-2-yl)-5-methyl-7-trifluoromethyl-imidazo[1,5-a][1,4]benzodiazepine-6(4H)-one Using the procedure of Example 1, the 5,6-dihydro-3-(1,3-dioxolan-2-yl)-5-methyl-7-trifluoromethylimidazo[1,5-a][1,4]benzodiazepine-6(4H)-one was obtained.

EXAMPLE 4

5,6-dihydro-5-methyl-3-(1,3-oxathiolan-2-yl)-7-trifluoromethyl-imidazo[1,5-a][1,4]benzodiazepine-6(4H)-one To a solution of 400 mg (1.29 mmol) of 5,6-dihydro-5-methyl-6-oxo-7-trifluoromethyl-4H-imidazo[1,5-a][1,4]benzodiazepine-3-carboxaldehyde in 12 ml of dichloromethane with 0.04 ml of boron trifluoroethate, there was added a solution of 0.18 ml (1.29 mmole) of 2-mercaptoethanol in 40 ml of dichloromethane dropwise over 5 hours. After 18 hours further 0.02 ml of boron trifluoroetherate was added and the reaction mixture was stirred for 24 hours at ambient temperature. The reaction mixture was extracted with aqueous sodium bicarbonate, water, dried over $MgSO_4$ and concentrated in vacuo to obtain a 47% yield of 5,6-dihydro-5-methyl-3-(1,3-oxathiolan-2-yl)-7-trifluoromethyl-imidazo[1,5-a][1,4]benzodiazepine-6(4H)-one after chromatography over silica gel.

Using the method of Example 4, the following compounds were prepared:

EXAMPLE 5

5,6-dihydro-5-methyl-3-(1,3-oxathiolan-2-yl)-imidazo[1,5-a][1,4]benzodiazepine-6(4H)-one

EXAMPLE 6

5,6-dihydro-7-fluoro-5-methyl-3-(1,3-oxathiolan-2-yl)-imidazo[1,5-a][1,4]benzodiazepine-6(4H)-one

TABLE I

[Structure: imidazole with R³ substituent, linked to benzene ring with CONHMe group and Z substituent]

| Ex. | R³ | Z | Yield | MP °C. | i.r. cm⁻¹ | ¹Hnmr | Formula M.Wt | Analysis: Calculated Found C | H | N | Other |
|---|---|---|---|---|---|---|---|---|---|---|---|
| 1 | (1,3-dioxolane) | H | 75.3% | 169-170 | 3650 3100(v.br);1630,1600,1490, 1420,1065,750 | CDCl₃ 8.05(1H,dd);7.87(1H,s);7.50(3H,m);5.96(1H,s); 4.50(1H,brd);4.20(1H,brd);4.10(4H,m);3.21(3H,d) | $C_{15}H_{15}N_3O_3$ 285.31 | 63.15 62.85 | 5.30 5.34 | 14.73 14.61 | |
| 2 | (1,3-dithiolane) | H | 75.6% | 158-160 Et₂O | 3100,2960,2930,1620,1495,1390,1230 940,760 | CDCl₃ 8.02(1H,dd);7.65(1H,s);7.35-7.57(3H,m);5.80(1H,s); 4.60(1H,brs);4.41(2H,brs);3.61(2H,m);3.40(4H,m); 3.28(3H,s) | $C_{15}H_{15}N_3OS_2$ 317.44 | 56.76 56.82 | 4.76 4.83 | 13.24 13.09 | S:20.21 20.16 |
| 3 | (1,3-dioxolane) | CF₃ | 60% | 202 | 3090,2900,1645,1600,1500,1470,1420 1395,1320,1310,1245,1185,1160,1130 1100,1085,1065,1010,955,830,820, 770,720,710,690,655 | δ(CDCl₃)3.17(3H,s);4.15(4H,mult);4.32(1H,d,J=16Hz); 4.61(1H,d,J=16Hz);5.95(1H,s);7.54(1H,d,J=8Hz); 7.70(1H,trip,J=8Hz);7.83(1H,d,J=8Hz);7.91(1H,s) | $C_{10}H_{14}N_3F_3O_3$ 353.99 | 54.39 54.04 | 4.00 4.00 | 11.89 11.80 | 16.13 16.18 |
| 4 | (1,3-dioxolane)/S | CF₃ | 47% | 200-201 | 3090,2900,1645,1495,1470,1425,1390 1320,1190,1155,1130,1095,1080,1055 965,935,825,810,770,730,710,690 and 655 cm⁻¹ | δ(CDCl₃)3.16 and 3.21(3H,2 singlets);3.31(2H,mult); 3.96(1H,mult);4.33(1H,dd,J=1.7,16Hz);4.66(2H,mult); 6.20 and 6.22(1H,2 singlets);7.73(3H,mult); 7.88 and 7.89(1H,2 singlets) | $C_{16}H_{14}N_3F_3O_2S$ 369.99 | 52.03 51.98 | 3.83 3.86 | 11.37 11.36 | 15.43 15.27 |
| 5 | (1,3-oxathiolane) | H | 26% | 171-172 | 3550,3380,3090,2920,2860,1635,1595 1580,1490,1430,1390,1290,1245,1220 1150,1060,1010,970,930,905,880,855 820,790,760,720,695 | 3.33(5H,m);3.69(1H,mult);4.52(3H,mult);6.22(1H,s); 7.38(1H,mult);7.55(2H,mult);7.84(1H,s);8.04(1H,s). | $C_{15}H_{15}N_3O_2S$ 301.36 | Accurate Mass Calc 301.0883 Found 301.0857 | | | |
| 6 | (1,3-oxathiolane) | F | 37% | 198-201 | 3105,2940,2860,1635,1590,1580,1490 1470,1435,1400,1290,1255,1220,1150 1055,1045,1020,965,940,915,875,805 770,730,695 and 660 | 3.31(5H,mult);3.97(1H,mult);4.36(1H,mult);4.58(2H,mult); 6.19 and 621(1H,singlets);7.22(2H,mult);7.56(1H,mult); 7.86(1H,s). | $C_{15}H_{14}N_3F_1S_1$ 319.36 | Accurate Mass Calc 319.0789 Found 319.0774 | | | |

EXAMPLE 7

Tablets were prepared containing 200 mg of the product of Example 1 or 2 or 4 or 6 and sufficient excipient of lactose, starch, talc and magnesium stearate for a final tablet weight of 150 mg.

Biochemical Activity

Test 1

The affinity of the active ingredients for the benzodiazepine receptors was measured using a radioactively labelled ($^3$H) compound, flunitrazepam, in a modified version of the method of Squires et al (*Nature*, 1977, Vol. 266, p. 732). The values given in Table 2 below are the concentration (mol×10$^{-9}$) of the test compound which inhibited 50% of the specific binding of 0.6×10$^{-9}$ mol of $^3$H-labelled flunitrazepam in preparation of membranes from the rear portion of the brain in rats (IC$_{50}$ values).

Test 2

Measurement of in vivo binding to benzodiazepine receptors was carried out according to the method described by Goeders at al., Life Sciences (1985) Vol. 37, p. 345.

TABLE 2

| Example | Test 1 nM | Test 2 ED$_{50}$ mg/kg ip |
| --- | --- | --- |
| 1 | 1075 | 1.0 |
| 2 | 94 | 7.0 |
| 3 | 73 | 0.09 |
| 4 | 10 | 0.08 |
| 5 | 339 | 0.8 |
| 6 | 36 | 0.22 |

Various modifications of the compounds and method of the invention may be made without departing from the spirit or scope thereof and it is to be understood that the invention is intended to be limited only as defined in the appended claims.

What we claim is:

1. A compound selected from the group consisting of a compound of the formula

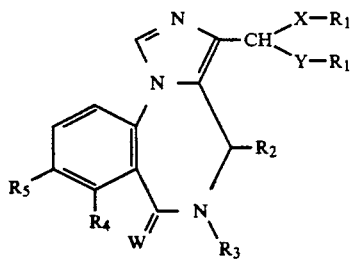

wherein the R$_1$s are the same and are alkyl of 1 to 3 carbon atoms or together are alkylene of 2 to 5 carbon atoms, X, Y and W are individually —O— or —S—, R$_2$ is hydrogen or alkyl of 1 to 3 carbon atoms, R$_3$ is selected from the group consisting of hydrogen, alkyl of 1 to 5 carbon atoms and phenyl optionally substituted with at least one member of the group consisting of halogen, alkyl and alkoxy of 1 to 3 carbon atoms and —CF$_3$, R$_4$ and R$_5$ are individually selected from the group consisting of hydrogen, halogen, —OH, alkyl and alkoxy of 1 to 3 carbon atoms and —CF$_3$ with the proviso that when R$_1$ and R$_2$ are alkyl, X and Y are the same and their non-toxic, pharmaceutically acceptable acid addition salts.

2. A compound of claim 1 wherein W is —O—, R$_2$ and R$_5$ are hydrogen and R$_4$ is halogen or —CF$_3$.

3. A compound of claim 1 wherein R$_3$ is methyl.

4. A compound of claim 1 selected from the group consisting of
5,6-dihydro-3-(1,3-dioxolan-2-yl)-5-methyl-imidazo-[1,5-a][1,4]-benzodiazepine-6(4H)-one;
5,6-dihydro-3-(1,3-dithiolan-2-yl)-5-methyl-imidazo[1,5-a][1,4]benzodiazepine-6(4H)-one;
5,6-dihydro-3-(1,3-dioxolan-2-yl)-5-methyl-7-trifluoromethyl-imidazo[1,5-a][1,4]benzodiazepine-6(4H)-one;
5,6-dihydro-5-methyl-3-(1,3-oxathiolan-2-yl)-7-trifluoromethyl-imidazo[1,5-a][1,4]benzodiazepine-6(4H)-one;
5,6-dihydro-5-methyl-3-(1,3-oxathiolan-2-yl)-imdiazo[1,5-a][1,4]benzodiazepine-6(4H) one;
5,6-dihydro-7-fluoro-5-methyl-3-(1,3-oxathiolan-2-yl)-imidazo[1,5-a][1,4]benzodiazepine-6(4H)-one and their non-toxic, pharmaceutically acceptable acid addition salts.

5. A composition for inducing benzodiazepine inverse agonist activity comprising an effective amount of at least one compound of claim 1 and an inert carrier.

6. A composition of claim 5 wherein in the compound of claim 1 W is —C—, R$_2$ and R$_5$ are hydrogen and R$_4$ is halogen or —CF$_3$—.

7. A composition of claim 5 wherein in the compound of claim 1 R$_3$ is methyl.

8. A composition of claim 5 wherein the active compound is selected from the group consisting of
5,6-dihydro-3-(1,3-dioxolan-2-yl)-5-methyl-imidazo-[1,5-a][1,4]-benzodiazepine-6(4H)-one;
5,6-dihydro-3-(1,3-dithiolan-2-yl)-5-methyl-imidazo[1,5-a][1,4]benzodiazepine-6(4H)-one;
5,6-dihydro-3-(1,3-dioxolan-2-yl)-5-methyl-7-trifluoromethyl-imidazo[1,5-a][1,4]benzodiazepine-6(4H)-one;
5,6-dihydro-5-methyl-3-(1,3-oxathiolan-2-yl)-7-trifluoromethyl-imidazo[1,5-a][1,4]benzodiazepine-6(4H)-one;
5,6-dihydro-5-methyl-3-(1,3-oxathiolan-2-yl)-imdiazo[1,5-a][1,4]benzodiazepine-6(4H)-one;
5,6-dihydro-7-fluoro-5-methyl-3-(1,3-oxathiolan-2-yl)-imidazo[[1,5-a][1,4]benzodiazepine-6(4H)-one and their non-toxic, pharmaceutically acceptable acid addition salts.

9. A method of inducing benzodiazepine inverse agonist activity in warm-blooded animals comprising administering to warm-blooded animals an amount of at least one compound of claim 1 sufficient to induce benzodiazepine inverse agonist activity.

10. A method of claim 9 wherein in the compound of claim 1 W is —O—, R$_2$ and R$_5$ are hydrogen and R$_4$ is halogen or —CF$_3$—.

11. A method of claim 9 wherein in the compound of claim 1 R$_3$ is methyl.

12. A method of claim 9 wherein the active compound is selected from the group consisting of
5,6-dihydro-3-(1,3-dioxolan-2-yl)-5-methyl-imidazo-[1,5-a][1,4]-benzodiazepine-6(4H)-one;
5,6-dihydro-3-(1,3-dithiolan-2-yl)-5-methyl-imidazo[1,5-a][1,4]-benzodiazepine-6(4H)-one;
5,6-dihydro-3-(1,3-dioxolan-2-yl)-5-methyl-7-trifluoromethyl-imidazo[1,5-a][1,4]benzodiazepine-6(4H)-one;

5,6-dihydro-5-methyl-3-(1,3-oxathiolan-2-yl)-7-trifluoromethyl-imidazo[1,5-a][1,4]benzodiazepine-6(4H)-one;

5,6-dihydro-5-methyl-3-(1,3-oxathiolan-2-yl)-imdiazo[1,5-a][1,4]benzodiazepine-6(4H)-one;

5,6-dihydro-7-fluoro-5-methyl-3-(1,3-oxathiolan-2-yl)-imidazo[1,5-a][1,4]benzodiazepine-6(4H)-one and their non-toxic, pharmaceutically acceptable acid addition salts.

* * * * *